(12) United States Patent
Pinnow

(10) Patent No.: US 10,959,778 B2
(45) Date of Patent: Mar. 30, 2021

(54) LASER SURGERY EMPLOYING HEAVY WATER TO ENHANCE LASER BEAM TRANSMISSION

(71) Applicant: Douglas Arthur Pinnow, Lake Elsinore, CA (US)

(72) Inventor: Douglas Arthur Pinnow, Lake Elsinore, CA (US)

(73) Assignee: Douglas A. Pinnow, Oceanside, CA (US)

( * ) Notice: Subject to any disclaimer, the term of this patent is extended or adjusted under 35 U.S.C. 154(b) by 406 days.

(21) Appl. No.: 15/338,423

(22) Filed: Oct. 30, 2016

(65) Prior Publication Data

US 2017/0128134 A1     May 11, 2017

Related U.S. Application Data

(60) Provisional application No. 62/252,471, filed on Nov. 7, 2015.

(51) Int. Cl.
*A61B 18/24*     (2006.01)
*A61B 18/00*     (2006.01)
*A61B 18/22*     (2006.01)

(52) U.S. Cl.
CPC .... *A61B 18/24* (2013.01); *A61B 2018/00029* (2013.01); *A61B 2018/00035* (2013.01); *A61B 2018/00511* (2013.01); *A61B 2018/00547* (2013.01); *A61B 2018/00577* (2013.01); *A61B 2018/2272* (2013.01); *A61B 2218/002* (2013.01)

(58) Field of Classification Search
CPC .......... A61B 18/24; A61B 2018/00029; A61B 2018/00035; A61B 2018/00511; A61B 2018/00547; A61B 2018/00577; A61B 2018/2272; A61B 2218/002
USPC ......................................... 606/4–16; 128/898
See application file for complete search history.

(56) References Cited

U.S. PATENT DOCUMENTS

| | | | | |
|---|---|---|---|---|
| 5,312,399 A * | 5/1994 | Hakky | ........... | A61B 17/320758 606/14 |
| 5,437,660 A * | 8/1995 | Johnson | ................. | A61B 18/24 606/15 |
| 6,572,609 B1 * | 6/2003 | Farr | ..................... | A61B 18/245 128/898 |
| 6,942,657 B2 * | 9/2005 | Sinofsky | .............. | A61B 18/245 606/15 |

(Continued)

*Primary Examiner* — Joseph M Dietrich
(74) *Attorney, Agent, or Firm* — Douglas A. Pinnow

(57) ABSTRACT

This invention relates to enhancement of the delivery of laser beams to internal surgical sites by employing, where practical, heavy water rather than normal water as both the irrigation fluid and the laser beam transmission medium that fills some or all of the space between the distal tip of the optical fiber to the surgical site. The use of heavy water is advantageous for surgical procedures employing lasers operating in the wavelength range of 1.0 microns to 2.5 microns where heavy water is substantially more transparent than normal water. This range includes the commercially important semiconductor diode laser operating at 1.47 microns where the optical attenuation coefficient in heavy water is less than one hundredth of that in normal water. Due to the rather high cost of heavy water, methods are described for collecting and re-cycling heavy water used during laser surgery to mitigate this cost.

3 Claims, 4 Drawing Sheets

(56) References Cited

U.S. PATENT DOCUMENTS

| | | | |
|---|---|---|---|
| 8,025,661 B2* | 9/2011 | Arnold | A61B 18/24 606/19 |
| 2007/0038203 A1* | 2/2007 | McIntyre | A61B 18/22 606/14 |
| 2014/0046060 A1* | 2/2014 | Jones | C07B 59/00 544/271 |

* cited by examiner

LASER SURGERY EMPLOYING HEAVY WATER TO ENHANCE LASER BEAM TRANSMISSION

CROSS REFERENCES TO RELATED APPLICATIONS

This application claims the benefit of U.S. Provisional Patent Application Ser. No. 62/252,477 filed Nov. 7, 2015, titled IMPROVED APPARATUS AND METHODS FOR SIDE-FIRE OPTICAL FIBER DEVICE SUITABLE FOR MEDICAL APPLICATONS and U.S. Provisional Patent Application Ser. No. 62/252,471 filed Nov. 7, 2015, titled LASER SURGERY EMPLOYING HEAVY WATER TO ENHANCE LASER BEAM TRANSMISSION the contents of which are hereby incorporated by reference herein.

TECHNICAL FIELD AND INDUSTRIAL APPLICABILITY OF THE INVENTION

BACKGROUND OF THE INVENTION

Field of the Invention

This invention relates to enhancement of the delivery of laser beams to internal surgical sites such as enlarged prostate glands (caused by benign prostate hyperplasia, BPH) or kidney stones by employing, where practical, heavy water rather than normal water as both the irrigation fluid and the laser beam transmission medium that fills some or all of the space between the distal tip of the optical fiber to the surgical site. The use of heavy water is advantageous for surgical procedures employing lasers operating in the wavelength range of 1.0 microns to 2.5 microns where heavy water is substantially more transparent than normal water. A preferred wavelength range extends from 1.20 microns to 1.55 microns. This preferred range includes the commercially important semiconductor diode laser operating at approximately 1.47 microns where the optical attenuation coefficient in heavy water is less than one hundredth ($1/100$) of that in normal water.

Description of Related Art

Over the past several decades, internal surgery using relatively high power laser beams for cutting, cauterizing and ablating tissue (such as in enlarged prostate glands), or pulverizing deposits (such as kidney stones) has grown to be an important method for treating many patients suffering from various ailments. Typically, these laser procedures are accomplished by guiding the laser beam through a transparent optical fiber that is inserted into a hollow channel in a cystoscope or an endoscope. A comprehensive discussion of this technology as it relates to the important field of prostate treatment can be found in an article by Bach et al. titled "Laser Treatment of Benign Prostatic Obstruction: Basic and Physical Differences" (European Urology, pp 317-325, 2012).

In most cases, the laser beam exiting the fiber tip must still propagate a relatively short distance to reach the surgical site. Often, transmission over this short distance is complicated by the presence of blood or other body fluids that can attenuate the laser beam. To mitigate this problem, a flow of normal water or saline solution is often employed to irrigate (wash away) most or all of the blood, other body fluids, or surgical debris and thereby provide a relatively transparent pathway through the water or saline solution for the transmission of the laser beam. The irrigation flow can be maintained either by gravity feed or by pumping from a reservoir, external to the patient. This flow continues down a gap between the optical fiber and a loosely fitted cannula until it exits the gap near the region of the distal tip of the fiber. Alternatively, the irrigation flow can be provided by some other means through a cystoscope/endoscope or around it.

While irrigation with normal water or saline solution has proved to be beneficial to provide a more transparent pathway between the distal tip of the optical fiber and the surgical site, it is not the optimum solution for a substantial number of infrared lasers having beam wavelengths that are substantially attenuated by normal water or saline solution. For example, if a laser beam is attenuated by, say, 20% to 50% while propagating through the irrigation fluid, the power of the laser source must be increased by a reciprocal amount to ensure that the laser beam power reaching the surgical site is sufficient to accomplish the desired procedure. This means that if the laser beam is attenuated by, say, 50% while propagating through the irrigation fluid, the laser source power must be doubled (1 divided by 50%=2) to ensure sufficient power for the surgical procedure. This leads to a number of related issues. The higher the laser power, the more expensive and larger the laser becomes. Also, higher laser power often is accompanied by instabilities in the laser beam that are expensive to control. Further, if for any reason, the optical fiber breaks within the cystoscope/endoscope, the higher laser beam power is more likely to damage not only the optical fiber jacket but also the expensive cystoscope or endoscope as well.

In some cases, an alternative strategy has been employed for dealing with high optical attenuation in an irrigation fluid. It is possible, for example, to provide a sufficient amount of laser power in an infrared beam to vaporize any aqueous material in the beam's path. In this case, the density of the fluid between the fiber tip and surgical site can be substantially reduced by conversion into steam. This reduction in density is associated with a corresponding substantial reduction in optical absorption. However, control of the laser beam is more difficult in this case and damage to the hot fiber tip that is surrounded in steam becomes more likely. In addition, it is well known that a fiber tip-steam interface leads to much higher Fresnel reflections of the laser beam in and around the fiber tip, as compared with using a liquid irrigation fluid. And absorption of these reflections can lead to overheating of the fiber and possible damage to it. Another alternative is to make direct contact between the optical fiber tip and the surgical site (without transmission through an irrigation fluid). This strategy is fraught with problems relating to contamination of the fiber tip with surgical debris that can subsequently lead to overheating of the fiber tip. This can lead to failure of the fiber tip and/or the need for frequent replacement. And it is particularly annoying to a surgeon and risky for the patient to have to replace a fiber in the middle of a surgical procedure. (As a general rule, any event that protracts a surgical procedure tends to increase the morbidity rate.)

Clearly it would be advantageous to use an irrigating fluid that has high transparency, low toxicity, and reasonable cost to prolong the fiber's effective life. In this regard, it is conventional wisdom that normal water is the logical choice for an irrigating fluid. However if some other fluid were available that has higher transparence than normal water, low toxicity, and reasonable cost, its use in laser surgery would represent an advance in the state-of-the-art.

SUMMARY OF THE INVENTION

The inventor has determined that heavy water is, in fact, more transparent than normal water in infrared wavelength bands ranging from 1.0 microns to 2.5 microns where a number of lasers used for internal surgery operate. It would therefore be preferred to use heavy water as the irrigation fluid of choice for the output laser beams in this wavelength range provided that the heavy water is not toxic and that it is available at a reasonable cost. However, at the inception of this work, it was by no means clear that issues surrounding the toxicity and cost of heavy water could be favorably resolved.

Heavy water, with a chemical formula $D_2O$, is isotopically different from normal water with a chemical formula $H_2O$. The D in the formula for heavy water stands for deuterium, a heavy isotope of hydrogen, that is approximately twice as heavy as a normal hydrogen, H, atom. Both D and H atoms contain a single proton in their cores. However, the nucleus of the D atom contains a neutron as well that is not present in the nucleus of H. It is the presence of this neutron in D that makes it nearly twice as heavy as H.

While the chemical characteristics of D and H are nearly identical in most substances including water, there are minor differences in their physical properties. For example, the boiling point of $H_2O$ is well known to be 100 degrees C. while the boiling point of $D_2O$ is slightly higher at 101.4 degrees C. The greatest difference between D and H is their natural abundance. D is a substantially rarer isotope with only about 1 D atom for every 6400 H atoms found in nature. That means that about one in every 6400 water molecules in the ocean has one deuterium replacing one hydrogen to form a DHO molecule and one in every $(6,400)^2$, or approximately 41,000,000, water molecules in the ocean is found in its fully deuterated form, $D_2O$.

So, heavy water is rather rare compared to normal water and, in fact, there was little interest in it other than as a laboratory curiosity until the development of nuclear weaponry during the World War II. Germany followed a path to make substantial amounts of heavy water that would be helpful in the production of plutonium to make atomic bombs—while the United States chose a different approach.

And even today, the greatest use of heavy water is as a neutron moderator in nuclear reactors that convert unenriched uranium into plutonium. So, it is not surprising that a common myth has emerged that heavy water is radioactive and therefore highly toxic to humans and animals. However, this is far from the truth. In fact, the toxicity of heavy water is quite low. It is not radioactive and due to its low but natural occurrence, a human adult would typically have approximately 5.5 grams of heavy water in their body at any time. A patent issued to Liepins in 1991 (U.S. Pat. No. 5,233,269) relates to increasing the concentration of heavy water in the human body to treat hypertension (high blood pressure). The claims in this patent cover oral doses of up to 0.6 liters of heavy water per day. But, very high concentrations of heavy water have been reported to lead to dizziness, possibly due to low blood pressure. As a consequence, there can be safety issues if heavy water were to replace between 25% and 50% of a human being's total body water weight with heavy water and death may result above 50%. However, a typical adult's body contains approximately 32 liters of water and only about 1 to 2 liters would be introduced during, say, a typical BPH surgical procedure and most of that would be quickly eliminated by voiding through the urinary track during or immediately after the surgery. So, there would not be any toxicity issues related to such a surgical application Another rather broadly known fact about heavy water, which is true, is that the relative rarity of D as compared with H in nature makes heavy water quite expensive to refine form normal sea water or other aqueous sources. At present, one liter of pure heavy water costs somewhere in the range of $600 to $1,000 on the open market (volume discounts may reduce this cost somewhat). And since one to two liters of water (either heavy or normal) are required for irrigation during a typical laser surgical procedure, the cost for choosing the heavy water alternative would tend to limit its use to critical procedures. Fortunately, the inventor has made a conceptual breakthrough relating to cost associated with using of heavy water in support of laser surgery.

The breakthrough came during the course of studying how high purity heavy water is typically refined from natural water. This is accomplished in a series of relatively expensive processing steps that require a major investment in capital equipment. During this processing, the $D_2O$ concentration increases from its initial value of one part in 6,400 to around 10% to 20% of the total (one part in 10 or 5, respectively) often employing a commercially viable process known as the Gridler process (developed by the Germans during WW II) that relies on the difference in deuterium and hydrogen ion exchange rates between liquid water and hydrogen sulfide gas. Once the $D_2O$ concentration reaches the 10% to 20% level using the Gridler process or some other process, it can be further increased by a relatively inexpensive final step to produce high purity $D_2O$ by distillation that takes advantage of the difference in boiling points of $H_2O$ and $D_2O$ discussed above. Alternatively, the final step can be accomplished by electrolysis.

Here it should be noted that distillation could, in principle, be used for the entire separation/purification of heavy water from natural water. However, when starting with only one part D to 6,400 parts H in nature, the process would require boiling off 6,399 liters of $H_2O$ for every 1 liter of $D_2O$ that is produced. This would be quite expensive because the cost of energy (fuel) to boil off the 6,399 liters of normal water would be substantial. In contrast, starting with an intermediate concentration of $D_2O$, in the range of 20%, that can be achieved by the Gridler process, requires boiling off only 5 liters of normal water to produce one liter of pure heavy water.

The conceptual breakthrough in the cost for using heavy water in laser surgery came with the realization that once used it would be foolish to let the heavy water be discarded, for example, by flushing it down a drain. Rather, the used heavy water would likely have a $D_2O$ concentration of around, say, 20 to 50% or greater after being diluted by body fluids and normal water during the course of the surgery. But, at a concentration of 20 to 50%, or so, this used irrigation fluid could be easily collected and sent to a recycling center. The recycling process would likely be accomplished a central facility using a filtration step followed by a low energy distillation (or electrolysis) step that would be inherently inexpensive.

In this way, the unit cost for a liter of recycled heavy water would only be a small fraction of the cost to make a pristine liter of heavy water starting from natural water. Importantly, by taking advantage of re-cycling, the cost for the use of heavy water during laser surgery would be substantially more affordable. This suggests much broader application to laser surgery than might otherwise be considered.

BRIEF DESCRIPTION OF THE DRAWINGS

The above SUMMARY OF THE INVENTION as well as other features and advantages of the present invention will be more fully appreciated by reference to the following detailed descriptions of illustrative embodiments in accordance with the present invention when taken in conjunction with the accompanying drawings, wherein.

DETAILED DESCRIPTION OF THE DRAWINGS

Figure 1:
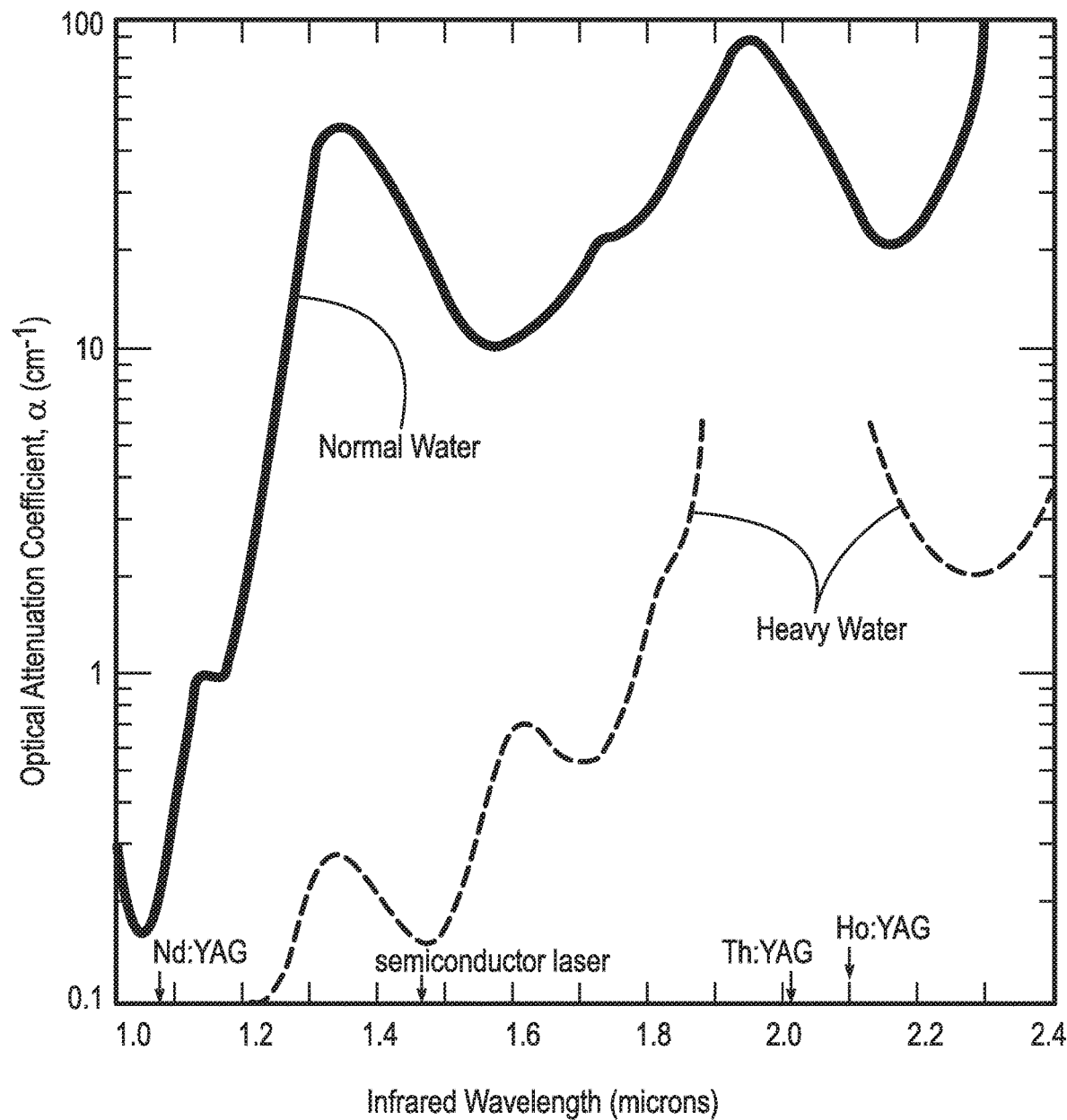
FIG. 1 is a graph showing the optical attenuation of normal water and heavy water as a function of optical wavelength.

FIG. 1 is a graph showing the optical attenuation of normal water and heavy water as a function of optical wavelength. The solid curve is for normal water. This curve for normal water has been reproduced from data available in the scientific literature. The dashed curve is for heavy water. This curve was developed from data taken by the inventor in the course of studying the effects of impurities, such as normal and heavy water, in highly transparent fused silica optical fibers. It should be noted that the infrared attenuation coefficient for heavy water in the wavelength range between 1.0 micron and 1.25 microns is below 0.1 cm$^{-1}$, but it is too low to be precisely measured by the equipment that was available at the time this data was acquired. That is why the lower limit for the ordinate shown in this graph is 0.1 cm$^{-1}$. It is important to recognize that any optical attenuation coefficients below 0.1 cm$^{-1}$ are sufficiently low that their effect on a surgical laser beam would be of only minor significance. The opposite is the case in the wavelength range of approximately 1.9 to 2.1 microns. In this range, the infrared attenuation coefficient exceeds 10 cm$^{-1}$ for heavy water and 30 cm$^{-1}$ for normal water making absorption so high that these wavelengths would not normally be employed for laser surgery unless optical attenuation in the irrigating fluid could be substantially reduced, for example, by converting this fluid into steam using the power in the laser beam. (See U.S. Patent Application No. 2009/004384 by Rink et al titled MULTI-WAVELENGTH LASER METHOD FOR CONTACT ABLATION OF TISSUE for more details on this strategy and the problems attendant with the use of steam.) The wavelengths for several different lasers used in surgery have been noted on the graph in FIG. 1 with arrows pointing to their operating wavelengths on the horizontal axis. This includes the Nd:YAG (neodymium doped yttrium aluminum garnet) laser operating at 1.064 microns, a semiconductor laser marked by Convergent Laser Technology that operates at 1.47 microns, a thulium doped fiber laser that operates at 1.949 microns, a Th:YAG (thulium doped yttrium aluminum garnet) laser that operates at 2.013 microns, and the Ho:YAG (holmium doped yttrium aluminum garnet) laser that operates at 2.10 microns.

The use of the semiconductor laser mentioned above that operates at 1.47 micron wavelength in conjunction with a heavy water irrigation fluid produces a favorable high tissue absorption coefficient of 20 cm$^{-1}$ (due to the high absorption coefficient of normal water that is contained in human tissue at this wavelength) along with a rather low absorption coefficient, of approximately 0.15 cm$^{-1}$ in the heavy water irrigation fluid through which the laser beam travels to reach the tissue. Such a high tissue absorption coefficient, for example in BPH surgery, is known to lead to a relatively shallow cauterization depth in the prostate tissue (approximately 0.5 to 1.0 mm) which is helpful in reducing patient recovery time. And the low absorption in the heavy water irrigation fluid results in the delivery of most all of the laser beam energy coming out of the fiber to the surgical site. In fact, use of a semiconductor laser, which is inherently efficient in converting electrical power to laser beam power, and having an output wavelength anywhere within the range of 1.20 to 1.55 microns would be beneficial for BPH surgical applications. Further, the 1.47 micron wavelength corresponds to a local minimum in the heavy water absorption spectrum making this wavelength an optimal choice. In fact, the use of a 1.47 micron semiconductor laser for BPH surgery in conjunction with a heavy water irrigation fluid may become preferred to the less efficient GreenLight Laser (a frequency doubled Nd:YAG laser operating at 0.532 microns) that has found broad acceptance in BPH surgery (see GreenLight XPS-180 Laser available from Boston Scientific, Inc.; www.bostonscientific.com).

While it is considered an advantage that the GreenLight laser can use normal water for the irrigation fluid because normal water is highly transparent at the green output wavelength (0.532 microns), the low efficiency of the GreenLight laser is a distinct disadvantage as compared to the 1.47 micron semiconductor laser. This low efficiency leads to a bulky and heavy laser module for the GreenLight laser. For example, a GreenLight laser used for BPH surgery weighs around 475 pounds, requires 240 Volt electrical input power, and water cooling. In comparison, a comparable 1.47 micron semiconductor laser weighs around 55 pounds, operates using 120 Volt electrical input power, and does not require water cooling (see T-1470 ProTouch Diode Laser System available from Convergent Laser Technologies, Inc., 1660 South Loop Road, Alameda, Calif. 94502).

Figure 2:
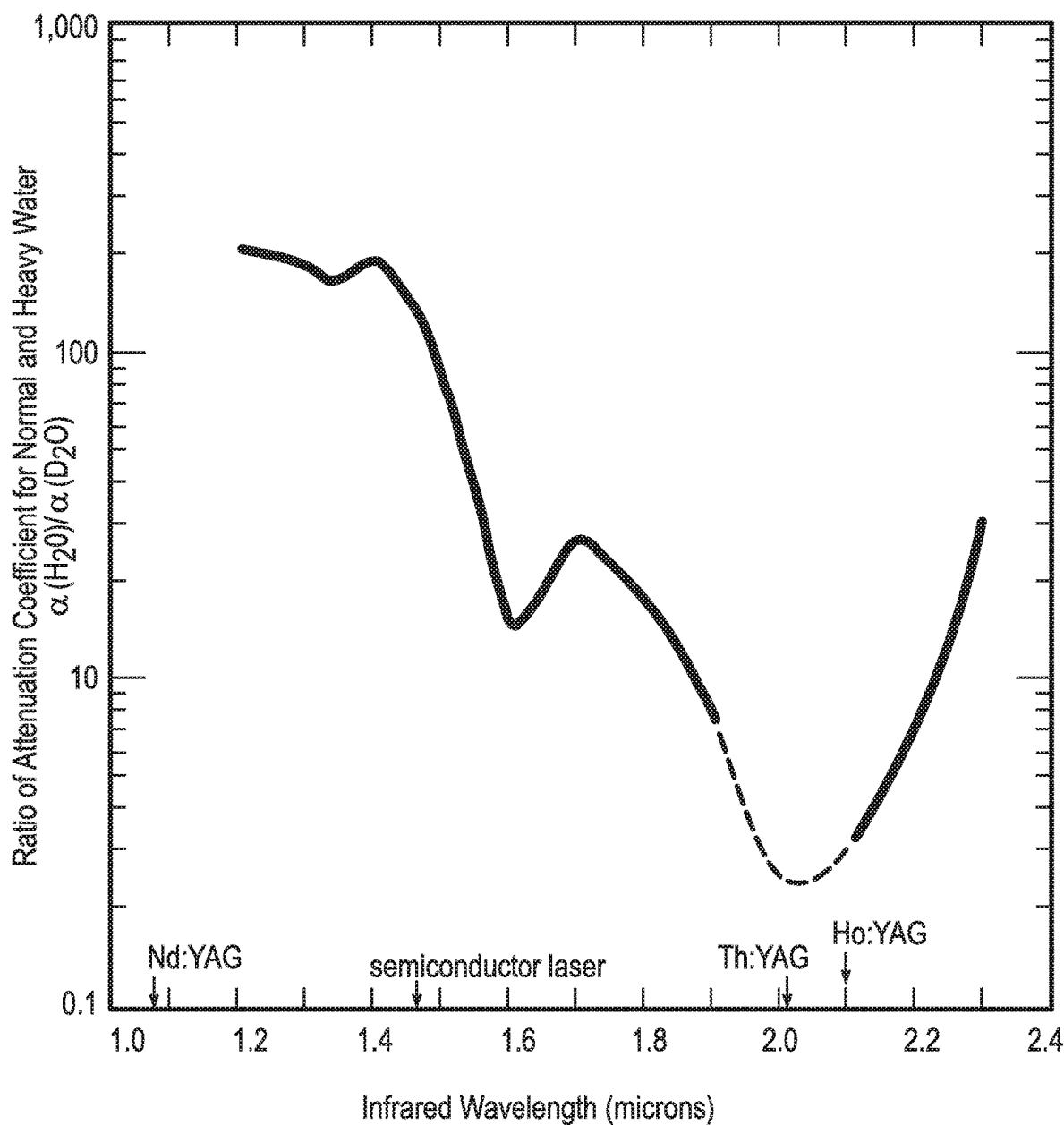
FIG. 2 is a graph showing the ratio of the optical absorption coefficient for normal water to that of heavy water as a function of infrared wavelength.

FIG. 2 is a graph showing the ratio of optical absorption coefficient for normal water to that of pure heavy water as a function of infrared wavelength. This graph is based on the reduction in data shown in FIG. 1. Its purpose is to emphasize the very substantial differences in the ratio of the optical absorption coefficient for normal water to that of heavy water throughout the entire 1.0 to 2.5 micron spectral range. This ratio is ranges from a factor of 3 to over 100. So, this is a very significant factor that allows an aqueous heavy water irrigation stream to remain in a liquid state (rather than being converted into steam due to the high absorption associated with normal water), provide cooling at the surgical site, provide refractive index matching to the glass fiber, and provide protection of the surgical fiber tip that enhances its useful operating lifetime. It should be mentioned that if heavy water and normal water were blended with an intermediated concentration (x % $D_2O$+(1-x) % $H_2O$), the optical attenuation of the mixture would be the concentration weighted sum of the optical attenuations in the two constituents (total attenuation=x % attenuation of $D_2O$ + (1-x) % attenuation of pure $H_2O$). To provide that greatest optical transparence for the irrigation fluid in the range of 1.0 to 2.5 microns would require the use of high concentration or pure heavy water having a $D_2O$ concentration of 98% or greater. Otherwise, even a relatively small percentage of normal water would have a deleterious effect on the low optical attenuation in pure $D_2O$. In this regard the term 'concentrated heavy water' in this paper will refer to heavy water with a $D_2O$ concentration of 98% or greater.

Figure 3A:
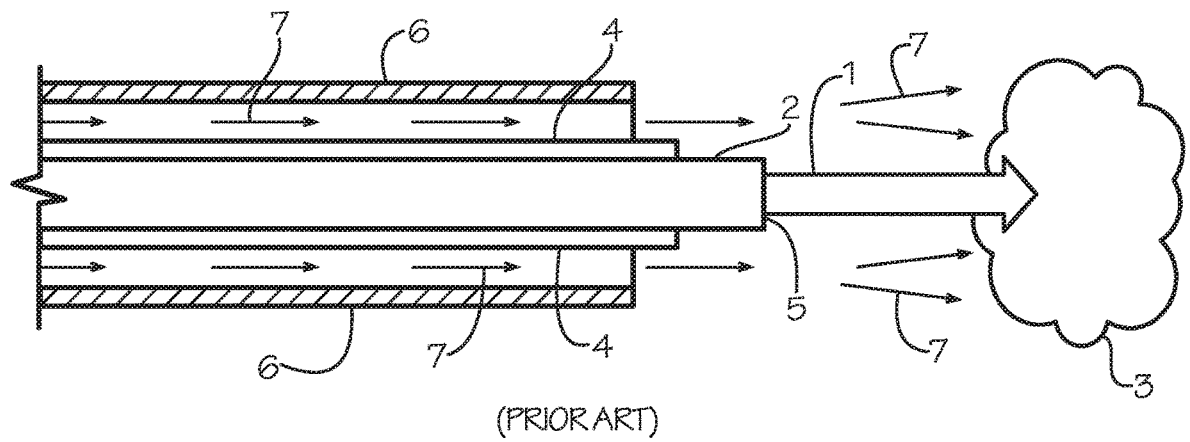
FIG. 3A shows a Prior Art design for a representative "end-fire" laser beam delivery device emphasizing the region in the vicinity of the distal tip of the optical fiber used in laser surgery.

FIG. 3A shows a Prior Art design for a representative "end-fire" laser beam delivery device emphasizing the region in the vicinity of the distal end of the optical fiber used in laser surgery. In this case, the laser beam 1 and optical fiber 2 have a common axis and the laser beam 1 is directed toward to a surgical site 3 (e.g. target tissue) directly in front of the fiber. The optical fiber 2 typically has a tight fitting plastic jacket 4 that is stripped back a short distance from the flat fiber end surface 5 that is normal to the axis of the fiber. Typically, the optical fiber 2 is contained in a loose fitting cannula 6 that is also used to transport irrigation fluid 7 (water or saline solution) to the surgical site 3. The irrigation fluid 7 that exits the cannula is generally directed around the distal end of the optical fiber to provide some beneficial cooling of the fiber end surface 5 as it fills the space between the fiber end surface 5 and the surgical site 3. After the laser beam exits the fiber end surface 5 it propagates substantially through the irrigation fluid 7 on its way to the surgical site 3.

Figure 3B:
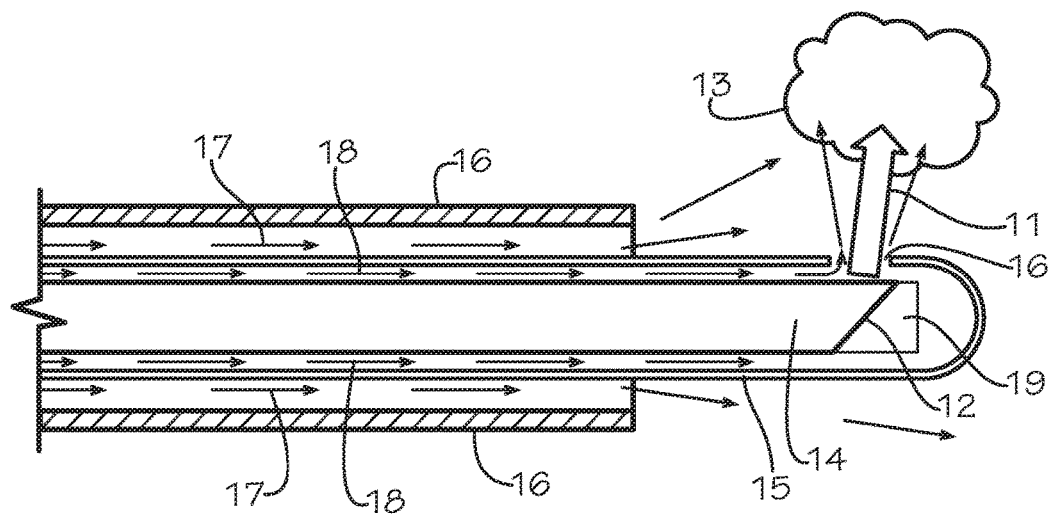
FIG. 3B shows a Prior Art design for a representative "side-fire" laser beam delivery device emphasizing the region in the vicinity of the distal tip of the optical fiber used in laser surgery.

FIG. 3B shows a Prior Art design for a representative "side-fire" laser beam delivery device emphasizing the region in the vicinity of the distal tip of an optical fiber used in laser surgery. This figure is based on the description in a patent application by Peng et al., Pub. No. US2009/0048599 dated Feb. 19, 2009. In this case, the laser beam 11 is re-directed by total internal reflection off of the beveled fiber end 12 that is inside of an air cavity 19 in a "side-fire" direction towards a surgical site 13 that is located to the side of the optical fiber. The optical fiber 14 in this example is contained in a loose fitting circular steel jacket 15 that has a penetrating hole 16 that serves as a port through which the surgical laser beam may pass. The steel jacket 15/optical fiber 14 assembly, in turn, fits inside of a cannula 16. The space between the inner wall of the cannula 16 and the outer surface of the steel jacket 15 is used to transport a primary stream of irrigation fluid 17 (water or saline solution) into the general area of the laser beam and the surgical site 13. In this example, a secondary stream of irrigation fluid 18 (water or saline solution) flows in the space between the optical fiber 14 and the inner surface of the steel tube 15. This secondary flow provides some beneficial cooling of the fiber tip before exiting through the penetrating hole 16 in the steel jacket 15. The flow then continues in the general direction of the surgical site 13. After the laser beam exits the penetrating hole 16 it propagates substantially through the irrigation fluid, provided by both streams of irrigation fluid 17 and 18, on its way to the surgical site 13.

Figure 4:
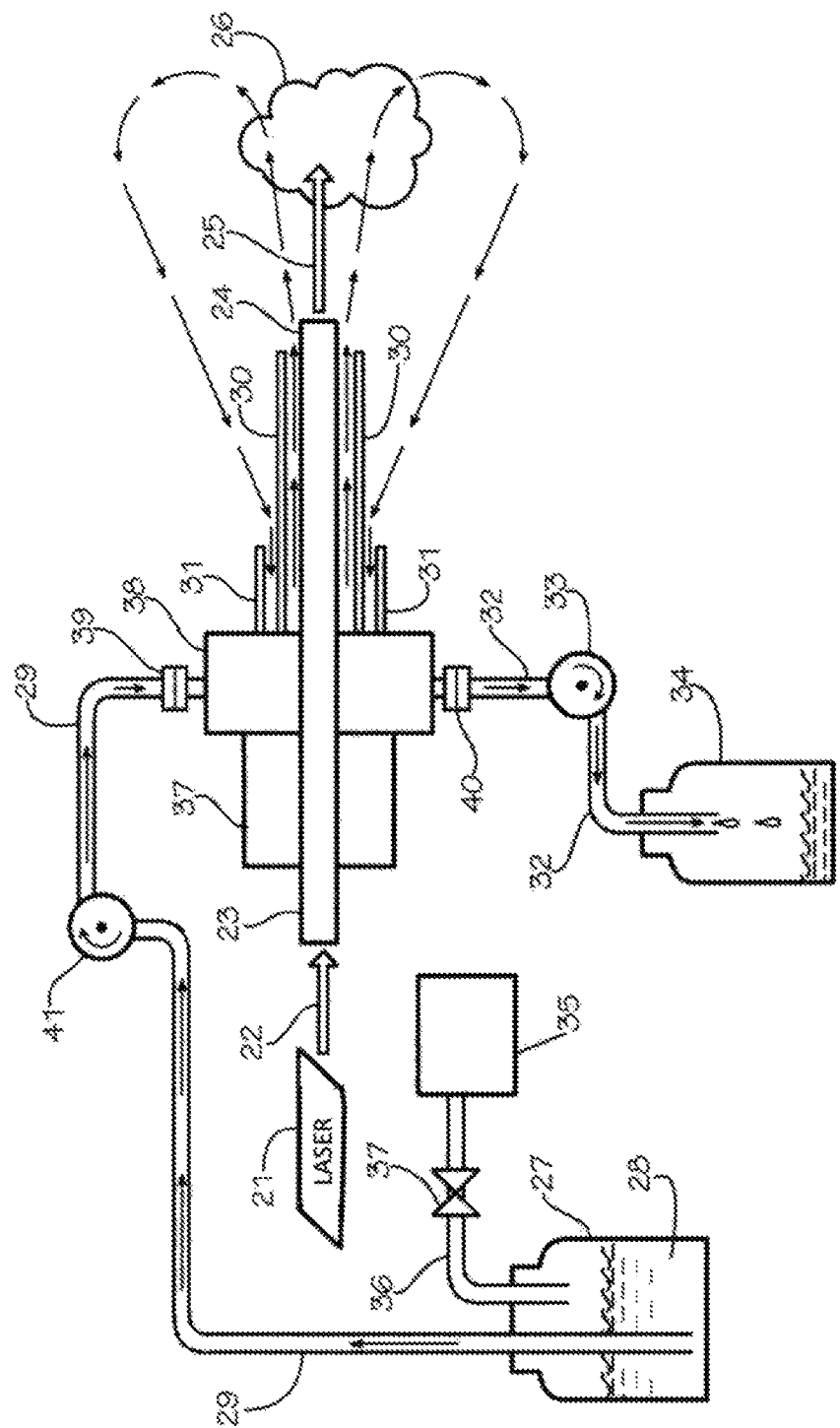
FIG. 4 is a schematic of the equipment set-up for performing laser surgery with a collection means for recovering used irrigation fluid

FIG. 4 shows a schematic of the equipment set-up for performing laser surgery with a collection means for recovering used irrigation fluid. Such recovery would be particularly desirable in cases where the irrigation fluid contains a substantial concentration of heavy water that has a high value. The laser source 21 has an output beam 22 that enters the proximal end of the optical fiber 23 and travels to the distal end of the fiber 24 where it exits the fiber. The output laser beam 25 is then directed to the surgical site 26 by the surgeon with the aid of a hand piece 37. Source container 27 contains a clean source of irrigation fluid 28 that can be moved out of the container 27 either with a source pump 41 (as shown) or by gravity feed (not shown) to flow through output tubing 29 and through the primary cannula 30. After this irrigation fluid 28 passes out of the primary cannula 30, it bathes the region between the distal end of the optical fiber 24 and the surgical site 26 before returning through a secondary cannula 31 and return tubing 32 with the aid of return pump 33 (as shown) or syphoning (not shown) to a recovery reservoir 34. Alternatively, the source pump 41 may be replaced by a source of pressurized air 35 that is directed to the source container 27 through tubing 36 and a valve 37. In this case, the air pressure over the irrigation fluid in the source container 27 would force a stream of irrigation fluid to flow towards the surgical site 26 through the output tubing 29 provided. The output tubing 29 connects to the irrigation fluid flow hub 38 through fluid connector 39 while the return flow of irrigation fluid is coupled from the flow hub 38 to the return tubing 32 through fluid connector 40. Alternate methods for recovering used irrigation fluid can be used either independently or in conjunction with the method described above. For example, immediately after surgery in the urinary system is completed, the patient may be fitted with a catheter and portable recovery bag to catch irrigation fluid remaining in the patient's bladder.

While the above disclosure describes how heavy water can be beneficially used in some exemplary laser surgery procedures, these examples should merely be considered to be representative of many others. It is therefore to be understood that the scope of this invention is broader than methods and procedures described in the specification and following claims and that the apparatus and methods described herein relate broadly to the use of heavy water during any laser surgery procedure.

The invention claimed is:

1. A method of performing urological surgery comprising the steps of (1) placing concentrated heavy water in all of the available space between a distal tip of an optical fiber transporting a laser beam and a surgical site, or a portion thereof, such that the concentrated heavy water contacts tissue of the surgical site, (2) directing all of said concentrated heavy water, or some portion thereof, to flow between the distal tip of the optical fiber transporting the laser beam and the surgical site, (3) collecting and recovering the concentrated heavy water after it passes through of the space between the distal tip of the optical fiber transporting a laser beam and the surgical site, and (4) using the collected and recovered concentrated heavy water in a laser surgery procedure.

2. A method according to claim 1 wherein said concentrated heavy water used in step (1) has been recovered after a previous laser surgery.

3. A method according to claim 2 wherein said concentrated heavy water used in step (1) has been recovered by the processes of filtration and distillation or by the processes of filtration and electrolysis.

* * * * *